US00PP28841P3

(12) United States Plant Patent
Bernuetz

(10) Patent No.: US PP28,841 P3
(45) Date of Patent: Jan. 2, 2018

(54) ***EUPHORBIA* PLANT NAMED 'BONPRI 1069'**

(50) Latin Name: ***Euphorbia pulcherrima* Willd. ex Klotzsch×*Euphorbia cornastra***
Varietal Denomination: Bonpri 1069

(71) Applicant: Andrew Bernuetz, Silverdale (AU)

(72) Inventor: Andrew Bernuetz, Silverdale (AU)

(73) Assignee: Bonza Botanicals Pty. Ltd., Yellow Rock, NSW (AU)

( * ) Notice: Subject to any disclaimer, the term of this patent is extended or adjusted under 35 U.S.C. 154(b) by 40 days.

(21) Appl. No.: 14/999,328

(22) Filed: Apr. 25, 2016

(65) Prior Publication Data

US 2017/0311512 P1 Oct. 26, 2017

(51) Int. Cl.
*A01H 5/02* (2006.01)

(52) U.S. Cl.
USPC ..... Plt./302

(58) Field of Classification Search
USPC ..... Plt./302
See application file for complete search history.

*Primary Examiner* — Keith Robinson
(74) *Attorney, Agent, or Firm* — C. A. Whealy

(57) ABSTRACT

A new and distinct cultivar of *Euphorbia* plant named 'Bonpri 1069', characterized by its compact, upright and mounded plant habit; vigorous growth habit; freely branching habit; dark green-colored leaves; freely flowering habit; inflorescences with light pink-colored flower bracts; and good post-production longevity.

1 Drawing Sheet

Botanical designation: *Euphorbia pulcherrima* Willd. ex Klotzsch×*Euphorbia cornastra.*

Cultivar denomination: 'BONPRI 1069'.

CROSS-REFERENCED TO CLOSELY-RELATED APPLICATIONS

Title: *Euphorbia* Plant Named 'BONPRI 1049'
Applicant: Andrew Bernuetz
Filed: Concurrently with this application

BACKGROUND OF THE INVENTION

The present invention relates to a new and distinct cultivar of *Euphorbia* plant, an interspecific hybrid botanically known as *Euphorbia pulcherrima* Willd. ex Klotzsch×*Euphorbia cornastra*, and hereinafter referred to by the cultivar name 'Bonpri 1069'.

The new *Euphorbia* plant is a product of a planned breeding program conducted by the Inventor in Yellow Rock, New South Wales, Australia. The objective of the program is to create and develop new interspecific *Euphorbia* plants with compact, upright and mounded plant habit and attractive flower bracts.

The new *Euphorbia* plant is a naturally-occurring whole plant mutation of *Euphorbia pulcherrima* Willd. ex Klotzsch×*Euphorbia cornastra* 'Bonpri 515', disclosed in U.S. Plant Pat. No. 25,587. The new *Euphorbia* plant was discovered and selected by the Inventor as a single flowering plant from within a population of plants of 'Bonpri 515' in a controlled greenhouse environment in Yellow Rock, New South Wales, Australia on Mar. 1, 2012.

Asexual reproduction of the new *Euphorbia* plant by terminal vegetative cuttings in a controlled greenhouse environment in Yellow Rock, New South Wales, Australia since March, 2012 has shown that the unique features of this new *Euphorbia* plant are stable and reproduced true to type in successive generations of asexual reproduction.

SUMMARY OF THE INVENTION

Plants of the new *Euphorbia* have not been observed under all possible combinations of environmental conditions and cultural practices. The phenotype may vary somewhat with variations in environmental conditions such as temperature, daylength and light intensity, without, however, any variance in genotype.

The following traits have been repeatedly observed and are determined to be the unique characteristics of 'Bonpri 1069'. These characteristics in combination distinguish 'Bonpri 1069' as a new and distinct *Euphorbia* plant:

1. Compact, upright and mounded plant habit.
2. Vigorous growth habit.
3. Freely branching habit.
4. Dark green-colored leaves.
5. Freely flowering habit.
6. Inflorescences with light pink-colored flower bracts.
7. Good post-production longevity.

In side-by-side comparisons conducted in Yellow Rock, New South Wales, Australia, plants of the new *Euphorbia* differ primarily from plants of the mutation parent, 'Bonpri 515' in the following characteristics:

1. Plants of the new *Euphorbia* are more compact than plants of 'Bonpri 515'.
2. Plants of the new *Euphorbia* are more freely branching than plants of 'Bonpri 515'.
3. Plants of the new *Euphorbia* have smaller leaves than plants of 'Bonpri 515'.
4. Plants of the new *Euphorbia* are more freely flowering than plants of 'Bonpri 515'.
5. Inflorescences of plants of the new *Euphorbia* have fewer flower bracts than inflorescences of plants of 'Bonpri 515'.

6. Plants of the new *Euphorbia* and 'Bonpri 515' differ in flower bract color as plants of 'Bonpri 515' have bright red purple-colored flower bracts.

Plants of the new *Euphorbia* can be compared to plants of the *Euphorbia pulcherrima* Willd. ex Klotzsch×*Euphorbia cornastra* 'Bonpri 1049', disclosed in U.S. Plant patent application Ser. No. 14/999,327. In side-by-side comparisons, plants of the new *Euphorbia* differ primarily from plants of 'Bonpri 1049' in flower bract color as plants of 'Bonpri 1049' have bright red purple-colored flower bracts.

BRIEF DESCRIPTION OF THE PHOTOGRAPHS

The accompanying photographs illustrate the overall appearance of the new *Euphorbia* plant showing the colors as true as it is reasonably possible to obtain in colored reproductions of this type. Colors in the photographs may differ slightly from the color values cited in the detailed botanical description which accurately describe the colors of the new *Euphorbia* plant.

The photograph at the top of the sheet comprises a side perspective view of a typical flowering plant of 'Bonpri 1069' grown in a container.

The photograph at the bottom of the sheet is a close-up view of a typical inflorescence of 'Bonpri 1069'.

DETAILED BOTANICAL DESCRIPTION

Plants used in the aforementioned photographs and described herewith in detail were grown during the autumn in 12-cm containers in an outdoor nursery in Higashiomi, Shiga, Japan and under cultural practices typical of commercial *Euphorbia* production. During the production of the plants, day temperatures averaged 23° C. and night temperatures averaged 13° C. Plants were four months old when the photographs and the description were taken. In the following description, color references are made to The Royal Horticultural Society Colour Chart, Fourth Edition, 2007, except where general terms of ordinary dictionary significance are used.

Botanical classification: *Euphorbia pulcherrima* Willd. ex Klotzsch×*Euphorbia cornastra* 'Bonpri 1069'.

Parentage: Naturally-occurring whole plant mutation of *Euphorbia pulcherrima* Willd. ex Klotzsch×*Euphorbia cornastra* 'Bonpri 515', disclosed in U.S. Plant Pat. No. 25,587.

Propagation:

*Type*.—Terminal vegetative cuttings.

*Time to initiate roots, summer*.—About ten days at 18° C. to 25° C.

*Time to initiate roots, winter*.—About twelve days at 16° C. to 20° C.

*Time to produce a rooted young plant, summer*.—About three weeks at 18° C. to 25° C.

*Time to produce a rooted young plant, winter*.—About four weeks at 16° C. to 20° C.

*Root description*.—Fibrous; white in color.

*Rooting habit*.—Freely branching; medium density.

Plant description:

*Plant habit and form*.—Compact, upright and mounded plant habit; inverted triangle; inflorescences positioned above the foliar plane; vigorous growth habit.

*Plant height*.—About 24 cm.

*Plant diameter or spread*.—About 33 cm.

*Lateral branch description*.—Branching habit: Freely branching habit, about five lateral branches develop per plant. Length: About 18 cm. Diameter: About 4.9 mm. Internode length: About 1.8 cm. Aspect: Mostly upright to somewhat outward. Strength: Strong. Texture: Sparsely pubescent. Color: Close to 143B.

*Leaf description*.—Arrangement: Alternate, simple. Length: About 7.6 cm. Width: About 5.2 cm. Shape: Elliptic. Apex: Acuminate. Base: Rounded. Margin: Shallowly serrate; undulate. Venation pattern: Pinnate, reticulate. Texture and luster, upper and lower surfaces: Sparsely pubescent; rough; matte. Color: Developing leaves, upper surface: Close to darker than 137A. Developing leaves, lower surface: Close to 137B. Fully developed leaves, upper surface: Close to 137A; venation, close to 144B. Fully developed leaves, lower surface: Close to 137C; venation, close to 144D. Petioles: Length: About 2.7 cm. Diameter: About 2 mm. Texture, upper and lower surfaces: Sparsely pubescent. Color, upper surface: Close to 144A. Color, lower surface: Close to 144C.

Inflorescence description:

*Inflorescence type and habit*.—Inflorescences are compound corymbs of cyathia with numerous flower bracts subtending the cyathia; inflorescences positioned above the foliar plane.

*Quantity of inflorescences*.—Freely flowering habit; about six inflorescences develop per plant.

*Inflorescence diameter*.—About 19.9 cm.

*Inflorescence height*.—About 7.3 cm.

*Fragrance*.—None detected.

*Natural flowering season*.—Plants typically flower during the autumn and winter in Japan; inflorescence initiation and development can also be induced under artificial long nyctoperiod and short photoperiod conditions; early flowering habit, plants flower about 50 days under natural season conditions in Japan.

*Post-production longevity*.—Good post-production longevity; plants of the new *Euphorbia* maintain good substance and bract color for about seven weeks.

*Flower bracts*.—Quantity per inflorescence: About 21. Length, largest bracts: About 8.4 cm. Width, largest bracts: About 5 cm. Shape: Elliptic. Apex: Acuminate. Base: Rounded. Margin: Shallowly serrate; undulate. Texture, upper and lower surfaces: Sparsely pubescent; rugose. Aspect: Mostly horizontal. Venation pattern: Pinnate, reticulate. Color: Transitional bracts, upper surface: Close to 55C to 55D; towards the apex, close to 137B; margin, proximally, close to NN155A; margin, distally, close to 150D. Transitional bracts, lower surface: Close to 56A to 56B; towards the apex, close to 137D; margin, proximally, close to NN155A; margin, distally, close to 145D. Developing bracts, upper surface: Close to 54C; towards the apex, close to 54D; toward the base, close to 63B; margins, close to 145D. Developing bracts, lower surface: Close to 11C. Fully expanded bracts, upper surface: Close to 65B; venation, close to 144C; proximally along main vein, close to 65A; margins, close to 145D. Fully expanded bracts, lower surface: Close to 56C; towards the apex, close to 144C; margins, close to 150D; venation, close to 144D. Flower bract petioles: Length: About 9.8 mm. Diameter: About 1.7 mm. Texture, upper and lower surfaces: Pubescent. Color, upper and lower surfaces: Close to 144A.

*Cyathia*.—Quantity per corymb: About twelve. Diameter of cyathia cluster: About 1.2 cm. Height, individual cyathium: Very small and undeveloped. Diameter, individual cyathium: Very small and undeveloped. Shape, individual cyathium: Globose; sessile. Color: Close to N144C. Nectaries: None observed on plants of the new *Euphorbia*.

*Peduncles*.—None observed on plants of the new *Euphorbia*.

*Reproductive organs*.—None observed on plants of the new *Euphorbia*.

*Seeds and fruits*.—Seed and fruit production has not been observed on plants of the new *Euphorbia*.

Disease & pest resistance: Plants of the new *Euphorbia* have not been shown to be resistant to pathogens and pests common to *Euphorbia* plants.

Temperature tolerance: Plants of the new *Euphorbia* have been observed to tolerate temperatures ranging from about 8° C. to about 40° C.

It is claimed:

1. A new and distinct *Euphorbia* plant named 'Bonpri 1069' as illustrated and described.

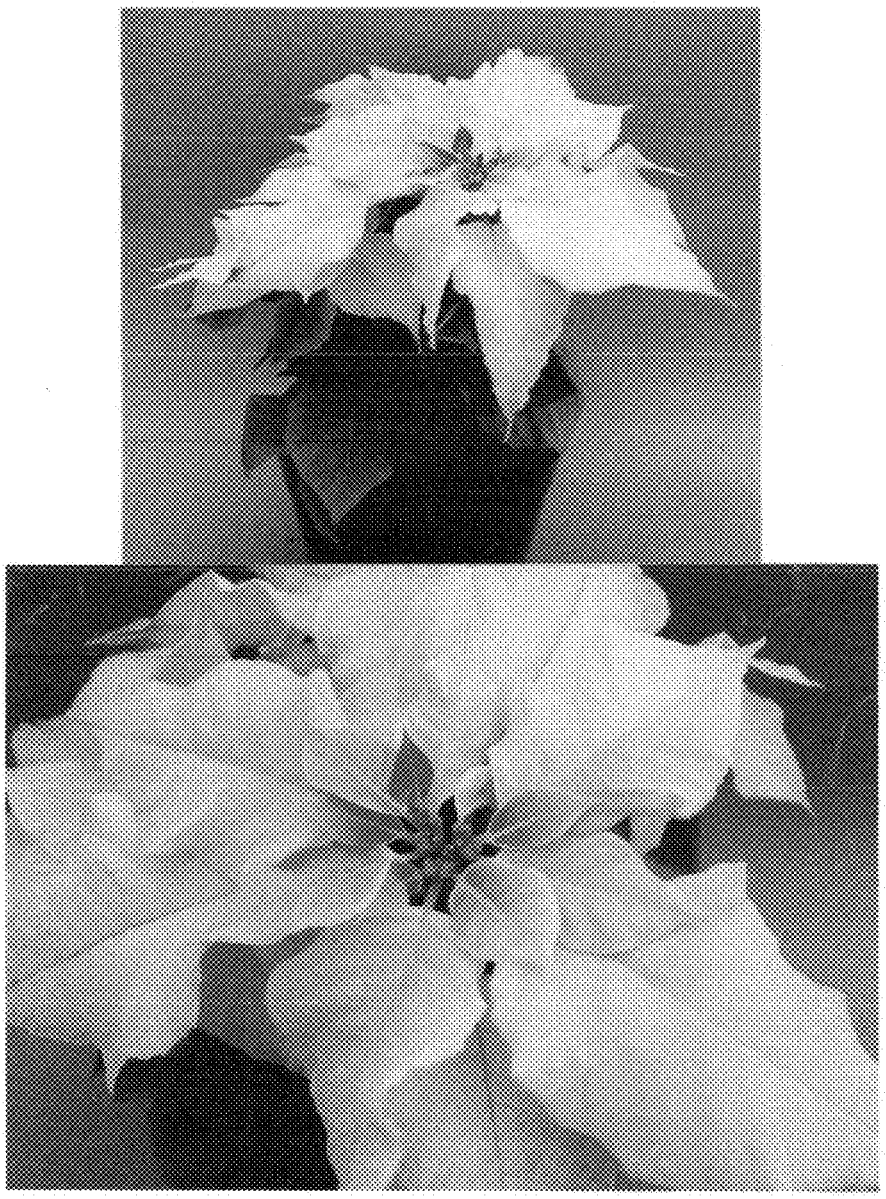

* * * * *